United States Patent [19]

Samain et al.

[11] Patent Number: 5,595,197
[45] Date of Patent: Jan. 21, 1997

[54] PROCESS FOR DIRECTLY COLORING KERATINOUS FIBRES USING SULPHONIC DYES AND WATER VAPOR

[75] Inventors: Henri Samain, Bievres; Jean-Michel Sturla, Saint-Cloud, both of France

[73] Assignee: L'Oreal, Paris, France

[21] Appl. No.: 356,955

[22] Filed: Dec. 16, 1994

[30] Foreign Application Priority Data

Dec. 22, 1993 [FR] France .................................. 93 15483

[51] Int. Cl.$^6$ ...................................... A61K 7/13
[52] U.S. Cl. .................................. 132/208; 8/405
[58] Field of Search .................................. 132/202, 203, 132/204, 205, 206, 207, 208, 209, 210, 211; 8/543, 588, 405

[56] References Cited

U.S. PATENT DOCUMENTS

| | | |
|---|---|---|
| 3,630,654 | 12/1971 | Rosenthal et al. . |
| 3,787,173 | 1/1974 | Greenshields et al. ...................... 8/163 |
| 4,166,473 | 9/1979 | Bauer et al. . |
| 4,341,229 | 7/1982 | Bauer et al. . |
| 4,348,204 | 9/1982 | Bauer et al. ................. 8/527 |
| 5,104,413 | 4/1992 | Ikeda ......................... 8/406 |

FOREIGN PATENT DOCUMENTS

| | | |
|---|---|---|
| 103547 | 3/1984 | European Pat. Off. . |
| 1011151 | 6/1952 | France . |
| 1157665 | 6/1958 | France . |
| 2273492 | 1/1976 | France . |

*Primary Examiner*—Todd E. Manahan
*Attorney, Agent, or Firm*—Finnegan, Henderson, Farabow, Garrett & Dunner, L.L.P.

[57] ABSTRACT

A process for directly dyeing keratinous fibres, characterized in that it comprises contacting the fibres with a composition containing at least one direct dye having at least one sulphonic functional group and with a gas containing water vapor, the temperature of the gas being at least 75° C. and the contact time between the gas and the fibres to be dyed not exceeding two minutes. This process makes it possible to obtain excellent dyeing results in extremely restricted time periods and without risk of substantially staining the skin or the scalp.

22 Claims, No Drawings

PROCESS FOR DIRECTLY COLORING KERATINOUS FIBRES USING SULPHONIC DYES AND WATER VAPOR

The present invention is directed to a process for directly colouring (or dyeing) keratinous fibres, in particular human keratinous fibres such as hair, using water vapour and a composition comprising direct dyes containing sulphonic functional groups.

Dyes known as direct dyes, that is, dyes which do not use an oxidation mechanism and which are capable of colouring keratinous fibres by themselves, are used to produce semi-permanent colourings. Direct dyes, by virtue of the variety of substances which can be used, make it possible to obtain a wide range of shades ranging from yellow to blue via red. Among direct dyes, dyes containing sulphonic groups are well known. Direct dyes containing sulphonic groups are particularly advantageous because they make it possible to obtain highly persistent dyeing. Hair treated with such direct dyes retains the effect of the colouring for a long time.

However, direct dyes containing sulphonic groups have a major disadvantage which limits their use. These dyes very readily stain the skin and in particular the scalp. Thus, if the colouring composition has been improperly applied or has flowed onto the scalp, the scalp, at the end of the colouring process of the head of hair (which usually requires a contact time of several tens of minutes), is highly and lastingly stained. Currently, only the skill of the hairdresser allows the staining of the scalp to be avoided or limited.

An object of the present invention is to solve this problem by using a reliable, simple, efficient and easily implemented process for directly colouring keratinous fibres. The process of the present invention makes it possible to avoid the disadvantages inherent in the use of sulphonic dyes, i.e., direct dyes containing sulphonic functional groups while retaining the advantages of such dyes.

It has been discovered that the use of a gas comprising water vapour, heated to a temperature of at least 75° C., preferably greater than 75° C., on hair treated with direct dyes containing sulphonic functional groups, makes it possible to obtain excellent dyeing results over short time periods and without the risk of substantially staining the skin or the scalp near or adjacent to the fibres being dyed. Keratinous fibres, in particular human keratinous fibres, treated in accordance with the present invention also have excellent cosmetic qualities following treatment. The process of the present invention also makes it possible to use sulphonic dyes in broader pH ranges, and in particular at a more basic pH than in the processes of the prior art.

The present invention is thus directed to a process for the direct dyeing of keratinous fibres, comprising the steps of: directly dyeing the fibres, the fibres having previously been contacted with a composition containing at least one direct dye containing a sulphonic functional group, by contacting the fibres with a gas containing water vapour, the gas having a temperature greater than 75° C., for a contact time between the gas and the fibres to be dyed less than two minutes.

The present invention is also directed to a process for the direct dyeing of keratinous fibres comprising the steps of: directly dyeing the fibres by contacting the fibres with a composition containing at least one direct dye containing a sulphonic functional group and with a gas containing water vapour, the temperature of the gas being at least 75° C., preferably greater than 75° C., and the contact time between the gas and the fibres being sufficient to dye the fibres without substantially staining the skin near or adjacent to the fibres.

The present invention further contemplates a process for the direct dyeing of keratinous fibres comprising the steps of: directly dyeing the fibres by contacting the fibres with a composition containing at least one direct dye containing a sulphonic functional group and with a gas containing water vapour, the temperature of the gas and the contact time between the gas and the fibres being sufficient to dye the fibres without substantially staining the skin near or adjacent to the fibres.

A further embodiment of the present invention includes a process for the direct dyeing of keratinous fibres comprising the steps of: directly dyeing the fibres by contacting the fibres with a composition containing at least one direct dye containing a sulphonic functional group and with a gas containing water vapour, for a time not exceeding two minutes, preferably less than two minutes, and wherein the gas has a temperature sufficient to dye the fibres without substantially staining the skin near or adjacent to the fibres.

A still further embodiment of the present invention includes a process for the direct dyeing of keratinous fibres, comprising the step of: directly dyeing the fibres by contacting the fibres with a composition containing at least one direct dye containing at least one sulphonic functional group and with a gas containing water vapour, the temperature of the gas being at least 75° C., preferably greater than 75° C., and the contact time between the gas and the fibres to be dyed not exceeding two minutes, preferably less than two minutes.

The process of the present invention is used for the direct dyeing of keratinous fibres in general. The preferred form of keratinous fibres taught by the present invention is human keratinous fibres such as hair.

The excellent results provided by the process of the present invention are all the more surprising since it is known that sulphonic dyes are sensitive to heat and that the staining effect mentioned above occurs more rapidly as the temperature increases. A person skilled in the art would therefore not be inclined to use sulphonic dyes in accordance with the present invention which can include use of a steam process.

The dyes containing sulphonic functional groups that are preferably be used in the present process may be chosen from the following compounds:

| | |
|---|---|
| (C.I. 10316) | 2,4-Dinitro-1-naphthol-7-sulphonic acid, sodium salt |
| (C.I. 10383) | Acid Orange 3 |
| (C.I. 13015) | Acid Yellow 9/Food Yellow 2 |
| (C.I. 14780) | Direct Red 45/Food Red 13 |
| (C.I. 13711) | Acid Black 52 |
| (C.I. 13065) | Acid Yellow 36 |
| (C.I. 14700) | 1-Hydroxy-2-(2',4'-xylyl-5-sulphonatoazo)naphthalene-4-sulfonic acid (sodium salt) (Food Red 1) |
| (C.I. 14720) | Acid Red 14/Food Red 3/Mordant Blue 79 |
| (C.I. 14805) | Acid Brown 4 |
| (C.I. 15510) | Acid Orange 7/Pigment Orange 17/Solvent Orange 49 |
| (C.I. 15985) | Food Yellow 3/Pigment Yellow 104 |
| (C.I. 16185) | Acid Red 27/Food Red 9 |
| (C.I. 16230) | Acid Orange 10/Food Orange 4 |
| (C.I. 16250) | Acid Red 44 |
| (C.I. 17200) | Acid Red 33/Food Red 12 |
| (C.I. 13683) | 1-(3'-Nitro-5'-sulpho-6'-oxophenylazo)-2-oxonaphthalene, Cr. Complex (Acid Red 184) |
| (C.I. 18055) | 1-Hydroxy-2-(4'-acetamidophenylazo)-8-acetamidonaphthalene-3,6-disulphonic acid (sodium salt) |

| | (Acid Violet 7/Food Red 11) |
|---|---|
| (C.I. 18065) | 1-Hydroxy-2-(2'-methylphenylazo)-8-acetamidonaphthalene-3,6-disulphonic acid (sodium salt) (Acid Red 35) |
| (C.I. 19125) | Acid violet 3 |
| (C.I. 18130) | Acid Red 135 |
| (C.I. 19130) | Acid Yellow 27 |
| (C.I. 19140) | Acid Yellow 23/Food Yellow 4 |
| (C.I. 20170) | 4'-(Sulphonato-2",4"-dimethyl)-bis-(2,6-phenylazo)-1,3-dihydroxybenzene (Acid Orange 24) |
| (C.I. 20470) | Acid Black 1 (Sodium salt of 1-amino-2-(4'-nitrophenylazo)-7-phenylazo-8-hydroxynaphthalene-3,6-disulphonic acid) |
| (C.I. 23266) | (4-((4-Methylphenyl)sulphonyloxy)-phenylazo)-2,2'-dimethyl-4-((2-hydroxy-5,8-disulphonato)naphthylazo)biphenyl (Acid Red 111) |
| (C.I 27755) | Food Black 2 |
| (C.I. 25440) | 1-(4'-Sulphonatophenylazo)-4-(2"-hydroxy-3"-acetylamino-6",8"-disulphonatonaphthylazo)-6-sulphonatonaphthalene (tetrasodium salt (Food Black 1) |
| (C.I. 42080) | 4-β-Hydroxyethylamino-3-nitrobenzenesulphonic acid |
| (C.I. 42090) | Acid Blue 9 |
| (C.I. 47005) | (5',6' or 7')-Sulphonato-6'-methylquinoline-2,2'-Δ-1,3-indanedione (Acid Yellow 3) |
| (C.I. 60730) | Acid Violet 43 |
| (C.I. 61570) | Acid Green 25 |
| (C.I. 62045) | Sodium salt of 1-amino-4-cyclohexanamino-9,10-anthraquinone-2-sulphonic acid (Acid Blue 62) |
| (C.I. 62105) | Acid Blue 78 |
| — | Acid Blue 156 |
| — | Acid Blue 317 |
| (C.I. 58005) | 1,2-Dihydroxy-3-sulphoanthraquinone (sodium salt) (Mordant Red 3) |
| (C.I. 62055) | 1-Amino-9,10-dihydro-9,10-dioxo-4-phenylamino-2-anthracenesulphonic acid, sodium salt |
| (C.I. 14710) | 4-Hydroxy-3-(2-methoxyphenylazo)-1-naphthalenesulphonic acid, sodium salt (Acid Red 4) 2-Piperidino-5-nitrobenzenesulphonic acid 2-(4'-N,N-(2"-Hydroxyethyl)amino-2'-nitro)anilinoethanesulphonic acid |

The majority of the above dyes are more particularly described in the Colour Index (published by The Society of Dyers and Colorists, P.O. Box 244, Perkin House, 82 Grattan Road, Bradford, Yorkshire, BD1 2JB, England). The more preferable sulphonic dyes that can be used are the dyes denoted under the code C.I. 60730, C.I. 15510, C.I. 47005, C.I. 15985, C.I. 17200, C.I. 20470, C.I. 42090, and C.I. 61570 in the Colour Index. The direct dye(s) containing sulphonic functional groups are generally present in concentrations ranging from 0.01% to 10% by weight with respect to the total weight of the composition.

The water vapour may be transported by a carrier gas that may additionally contain solvent vapour. As the vapour, gases such as oxygen or nitrogen, mixtures of gases such as air or other vapourizable compounds can be used.

The solvents which can be used for the production of vapour are cosmetically acceptable organic solvents such as alcohols, glycols or glycol ethers. Suitable alcohols include ethanol, isopropanol, benzyl alcohol and phenylethyl alcohol. Typical glycols or glycol ethers include the monomethyl, monoethyl, and monobutyl ethers of ethylene glycol, propylene glycol, butylene glycol, dipropylene glycol, and alkyl ethers such as the monobutyl ether of diethylene glycol.

The gas preferably comprises at least 1% by volume of water vapour with respect to the total volume of the gas. The gas preferably contains either exclusively or essentially water vapour or of a mixture of water vapour and air. The temperature of the gas is at least 75° C., preferably greater than 75° C. The temperature of the gas is more preferably at least 85° C. and even more preferably ranges from 85° C. to less than 150° C. Still more preferably, the temperature of the gas ranges from 85° C. to less than 100° C. Most preferably, the temperature of the gas ranges from 90° C. to less than 100° C.

The gas is contacted with the fibres to be dyed for a period of time preferably ranging from 0.01 second to less than 2 minutes. The gas is more preferably contacted with the fibres for a period of time ranging from 0.01 second to 30 seconds and most preferably from 0.5 to 10 seconds. Application of the gas can be repeated several times on the same fibres, with each application being conducted for a time period as prescribed above.

In a preferred embodiment of the process according to the invention, a hair-colouring composition containing sulphonic direct dyes is applied to the hair and the hair is subsequently subjected to the action of the water vapour. Another embodiment of the present inventive process contemplates applying simultaneously the colouring composition and the gas comprising water vapour. It is also possible to deliver all or part of the colouring composition to the hair using the gas flow when some or all the constituents of the formula can be entrained or evaporated. In a further embodiment of the invention, application of the water vapour is followed by rinsing with water.

The production of a hot gas comprising water vapour may be achieved using any apparatus known per se. Use is preferably made of an apparatus such as that described in French Patent Application FR-A-2,273,492 or its U.S. counterparts, U.S. Pat. Nos. 4,166,473 and 4,341,239, the disclosures of which, including the drawings, are incorporated by reference, or any other equivalent apparatus, which is particularly well suited (selective, even and homogenous treatment of the fibres, without risk of overheating).

If the dye has been contacted with the skin and/or the scalp, accidently or due to improper handling, the particularly short contact times of the present invention mean that the dye does not have time to be absorbed by the skin and/or the scalp, which greatly reduces if not totally eliminates both the risk and extent of staining.

The dyeing composition used in the process according to the invention may be provided in forms commonly used for dyeing hair, such as a more or less thickened or gelled liquid, cream, aerosol foam, or any other form appropriate for carrying out the dyeing of hair.

The compositions used in accordance with the invention are generally aqueous compositions which can contain ingredients commonly used in cosmetic compositions intended for colouring hair, such as solvents, surface-active agents, thickeners, treating agents, basifying of acidifying agents, preserving agents, fragrances or any other additive used in this type of composition.

The dyeing composition containing at least one dye containing a sulphonic functional group has a pH generally ranging from 2 to 11.

The example which follows illustrates the invention without in any way limiting the scope of the invention.

EXAMPLE

A dyeing composition was used which had the following characteristics:

| | | |
|---|---|---|
| Acid Black 1 | | 0.4 g |
| Benzyl alcohol | | 3 g |
| 1,3-Butylene glycol | | 10 g |
| Xanthan gum | | 1.5 g |
| Citric acid | q.s. | pH 3.5 |
| Water | q.s. for | 100 g |

The procedure used was as follows: the above defined composition was applied to the hair and the composition was deliberately allowed to flow onto the skin. A jet of water vapour at 90° C. was then directed onto a first part of the head of hair for 5 seconds. The hair and the skin were rinsed with water and then dried (Skin No. 1). On a second part of the head of hair, the composition was allowed to lie for 30 minutes at normal temperature. The hair and the skin were rinsed with water and then dried (Skin No. 2).

In both cases, the chromaticity coordinates L, a, and b of the skin before and after dyeing were measured (Minolta Chroma Meter CR 200 Colorimeter), which made it possible to compare the difference in the staining associated with each of the two processes.

$\Delta L$, $\Delta a$ and $\Delta b$ represent the differences, in absolute values, between the final L, a and b values (after colouring) and the initial L, a and b values (before colouring) of the skin.

| | $\Delta L$ | $\Delta a$ | $\Delta b$ |
|---|---|---|---|
| Skin No. 1 | 2.6 | 1.45 | 1.9 |
| Skin No. 2 | 14.2 | 8.5 | 10.2 |

It was noted that, with the use of the steam process according to the invention, i.e., Skin No. 1 process, the skin was appreciably less stained. In fact, the $\Delta L$, $\Delta a$ and $\Delta b$ values were much lower than those obtained with the conventional process.

What is claimed is:

1. A process for the direct dyeing of keratinous fibres comprising the step of:
   directly dyeing said fibres, said fibres having previously been contacted with a composition containing at least one direct dye containing a sulphonic functional group, by contacting said fibres with a gas containing water vapour, said gas having a temperature greater than 75° C., for a contact time between said gas and said fibres to be dyed less than two minutes.

2. A process according to claim 1, wherein the gas has a temperature of at least 85° C.

3. A process according to claim 2, wherein the gas has a temperature ranging from 85° to 150° C.

4. A process according to claim 1, wherein the gas is contacted with the fibres to be dyed for a period of time ranging from 0.01 second to less than 2 minutes.

5. A process according to claim 4, wherein the gas is contacted with the fibres to be dyed for a period of time ranging from 0.01 second to 30 seconds.

6. A process according to claim 5, wherein the gas is contacted with the fibres to be dyed for a period of time ranging from 0.5 second to 10 seconds.

7. A process according to claim 1, wherein the application of the gas is repeated several times on the fibres.

8. A process according to claim 1, wherein the gas contains exclusively water vapour.

9. A process according to claim 1, wherein the gas contains water vapour and at least one other compound in the form of gas or vapour.

10. A process according to claim 9, wherein the gas contains water vapour and air.

11. A process according to claim 1, wherein said at least one direct dye containing sulphonic functional groups is selected from the compounds denoted under the code C.I. 60730, C.I. 15510, C.I. 47005, C.I. 15985, C.I. 17200, C.I. 20470, C.I. 42090 and C.I. 61570 in the Colour Index.

12. A process according to claim 1, wherein said at least one direct dye containing sulphonic functional groups is present in concentrations ranging from 0.01% to 10% by weight with respect to the total weight of the composition.

13. A process according to claim 1, wherein the composition containing at least one direct dye containing a sulphonic functional group has a pH ranging from 2 to 11.

14. A process according to claim 1, wherein said keratinous fibres are human keratinous fibres.

15. A process according to claim 1, wherein said gas has a temperature ranging from 75° C. to less than 100° C.

16. A process according to claim 15, wherein said gas has a temperature ranging from 85° C. to less than 100° C.

17. A process according to claim 16, wherein said gas has a temperature ranging from 90° C. to less than 100° C.

18. A process for the direct dyeing of keratinous fibres comprising the step of:
   directly dyeing said fibres by contacting said fibres with a composition containing at least one direct dye containing a sulphonic functional group and with a gas containing water vapour, for a time not exceeding two minutes, and wherein said gas has a temperature sufficient to dye said fibres without substantially staining the skin adjacent to said fibres.

19. A process according to claim 18, wherein said keratinous fibres are human keratinous fibres.

20. A process for the direct dyeing of keratinous fibres comprising the steps of:
   directly dyeing said fibres by contacting said fibres with a composition containing at least one direct dye containing a sulphonic functional group and with a gas containing water vapour, said gas having a temperature of at least 75° C., for a contact time between said gas and said fibres to be dyed not exceeding two minutes.

21. A process according to claim 20, wherein said gas containing water vapour is contacted with said fibres subsequent to said fibres being contacted with a composition containing at least one direct dye containing a sulphonic functional group.

22. A process according to claim 20, wherein said gas containing water vapour is contacted with said fibres simultaneously with said fibres being contacted with a composition containing at least one direct dye containing a sulphonic functional group.

* * * * *